United States Patent
King

(10) Patent No.: US 9,980,629 B2
(45) Date of Patent: May 29, 2018

(54) VIDEO CAPTURE AND STREAMING DIAGNOSTICS METADATA

(71) Applicant: Karl Storz Imaging, Inc., Goleta, CA (US)

(72) Inventor: Timothy King, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 352 days.

(21) Appl. No.: 13/793,232

(22) Filed: Mar. 11, 2013

(65) Prior Publication Data

US 2014/0253703 A1  Sep. 11, 2014

(51) Int. Cl.
*G06F 19/00* (2018.01)
*A61B 1/00* (2006.01)

(52) U.S. Cl.
CPC ........ *A61B 1/00057* (2013.01); *G06F 19/321* (2013.01)

(58) Field of Classification Search
CPC ...... A61F 6/5258; A61F 6/545; G06F 19/321; G06F 19/322; G06Q 50/22; G06Q 50/24
See application file for complete search history.

(56) References Cited

U.S. PATENT DOCUMENTS

| | | | |
|---|---|---|---|
| 5,213,108 A * | 5/1993 | Bredesen | A61B 7/04 381/67 |
| 6,364,827 B1 | 4/2002 | Irion et al. | |
| 6,567,980 B1 * | 5/2003 | Jain et al. | 725/61 |
| 6,629,104 B1 * | 9/2003 | Parulski | G06F 17/30265 348/231.2 |
| 6,731,305 B1 * | 5/2004 | Park et al. | 345/629 |
| 7,133,546 B2 | 11/2006 | Dehmeshki et al. | |
| 7,289,139 B2 | 10/2007 | Amling et al. | |
| 7,630,006 B2 * | 12/2009 | DeLuca et al. | 348/241 |
| 7,722,531 B1 | 5/2010 | Boche | |
| 7,738,683 B2 | 6/2010 | Cahill et al. | |
| 8,194,122 B2 | 6/2012 | Amling et al. | |
| 8,311,847 B2 | 11/2012 | Kotula et al. | |
| 2002/0062380 A1 * | 5/2002 | Mohammed et al. | 709/228 |
| 2003/0005464 A1 * | 1/2003 | Gropper | G06F 19/321 725/115 |
| 2003/0108354 A1 * | 6/2003 | Guddanti | G06K 15/00 399/8 |
| 2004/0133923 A1 * | 7/2004 | Watson et al. | 725/134 |
| 2004/0141661 A1 * | 7/2004 | Hanna et al. | 382/305 |
| 2005/0002648 A1 * | 1/2005 | Hoshino | H04N 5/222 386/224 |
| 2005/0117029 A1 * | 6/2005 | Shiomi | H04N 5/372 348/222.1 |

(Continued)

OTHER PUBLICATIONS

DICOM homepage: http://dicom.nema.org/.*

(Continued)

*Primary Examiner* — Jay Patel
*Assistant Examiner* — Shadan E Haghani
(74) *Attorney, Agent, or Firm* — Whitmyer IP Group LLC

(57) ABSTRACT

A system and method for diagnosing problems in a medical imaging system. In some implementations, problems with the medical imaging system are determined by encoding information into an image relating to system settings or other data, and using the information to diagnose possible problems with the image and/or the medical imaging system.

60 Claims, 4 Drawing Sheets

(56) References Cited

U.S. PATENT DOCUMENTS

| | | | |
|---|---|---|---|
| 2005/0203771 A1* | 9/2005 | Achan | G06Q 10/103 705/2 |
| 2005/0225643 A1* | 10/2005 | Grignani | H04N 1/21 348/207.99 |
| 2007/0127833 A1* | 6/2007 | Singh | G06F 17/30265 382/254 |
| 2011/0110572 A1* | 5/2011 | Guehring | A61B 6/5258 382/131 |
| 2011/0164126 A1 | 7/2011 | Ambor et al. | |
| 2012/0200683 A1* | 8/2012 | Oshima | A61B 1/00009 348/65 |

OTHER PUBLICATIONS

M. Löbe, M. Knuth, R. Mücke "TIM: A Semantic Web Application for the Specification of Metadata Items in Clinical Research", CEUR-WS.org, urn:nbn:de:0074-559-9 (2009) 7 pages.
European Search Report Application No. EP 14 15 8648 Completed: Jan. 15, 2015; dated Jan. 30, 2015 5 pages.

\* cited by examiner

VIDEO CAPTURE AND STREAMING DIAGNOSTICS METADATA

FIELD OF THE INVENTION

The invention relates to a system and method for diagnosing problems in an imaging system, and more specifically to encoding information into an image relating to system settings or other data, and using the information to diagnose problems with the image.

BACKGROUND OF THE INVENTION

In modern times, medicine has come to rely on medical imaging in order to safely and effectively diagnose and treat ailments in humans and animals. Recent medical imaging techniques have allowed for safer and more effective medical images to be produced using newly available technologies.

Among these technological advances has been the incorporation of advanced digital imaging and image processing technologies that have arisen as a part of the computer and information revolution.

The latest endoscopes, for example, have advanced from the crude telescopes of the past into complex electro-mechanical devices. Modern endoscopic imaging systems may incorporate fiber-optic technologies, multiple wavelength illumination, channels for the introduction of surgical tools, charge-coupled image sensors, and computerized analysis systems.

However modern endoscopy systems can be particularly susceptible to damage or may otherwise be prone to deviations from normal operation. This is because of their complexity, and because endoscopes are exposed to harsh environments during normal use. For example, the operation of a modern endoscopy system may be impaired by kinetic shocks or operator error, such as improper positioning or setting of the device. Further, before and after insertion into a body cavity an endoscope must be sterilized. This may entail exposure to water, harsh cleaning solvents, corrosive gasses, or high temperatures. During use, an endoscope may be exposed to temperature or humidity gradients, electro-cautery equipment, radiation from imaging or therapeutic sources, or other environmental conditions. Any of these conditions can impair the operation of the endoscopy system.

While these modern systems make safer and more powerful diagnostic and therapeutic imaging possible, the complexity of such systems can cause difficulty in diagnosing the source of the problem when problems are found with an image produced by the system.

In more recent times, digital images have been encoded with additional non-image information as metadata. Typically, metadata includes information about the image, and may include information about the device which created the image. Several image metadata standards are known, including IPTC, XMP, EXIF, DCMI, and PLUS. However, no standard presently exists for medical imaging metadata.

In the past, metadata has been used only tangentially in medical imaging, and has not been used for system diagnostics.

U.S. Pat. No. 8,311,847 to Kotula et al. disclose a system for interfacing with multiple medical imaging modalities that includes a normalization module for normalizing hanging protocols for displaying the images. Effectively, the system uses metadata to organize the images for viewing. The system may analyze metadata associated with the images which includes equipment settings used to capture the information. A metadata extractor can extract the metadata from the images, in order to create manifest files. These manifest files are used to generate display rules for presenting the images in a normalized manner, in order to enable radiologists to work with images that are organized according to image and study semantics.

U.S. Pat. No. 7,738,683 to Cahill et al. disclose a system for analyzing a medical image for purposes of patient diagnosis. Various types of images and corresponding data are captured during a multi-modal examination. This information is fed into a learning engine that determines the characteristics of abnormalities in the medical images from different modalities, and a detecting engine that detects abnormalities within an image.

U.S. Pat. No. 7,133,546 to Dehmeshki et al. disclose a system for processing a digital medical image to identify medical abnormalities. Metadata associated with the image is used to derive optimum parameter values using a predetermined relationship between the metadata and the parameters. The medical image is then processed using the optimum parameter values and an algorithm in order to analyze the medical image for medical abnormalities.

However, no known system discloses or teaches the use of metadata to troubleshoot an endoscopy system or any other medical imaging system.

It is therefore desired to provide a system and method which overcomes these deficiencies.

SUMMARY OF THE INVENTION

While capturing still or video images, specific data may also be recorded or inserted into the files or streams as metadata. This metadata may include information such as part numbers and/or serial numbers of any or all of the devices attached to the system, and their associated software and hardware versions.

The metadata may include information about the current settings of the video system such as enhancement and brightness, various automatic parameters such as gain, exposure, light source level, and the like. This information provides clues as to the scenery conditions of an image, for example, during the recording and/or streaming of still and video images. Endoscope use data may also be included in the metadata, and other types of information may be included as further discussed herein.

The information included in the metadata allows the end-users to simply send an image file to customer service representatives and/or technicians who can use the metadata to more quickly determine the root cause of any non-optimal system performance. For example, a customer service representative can extract the metadata from a video recording of still image and quickly see if the software versions are up to date. As another example, a customer service representative could check to see if the settings were not optimal for the scenario and suggest other settings. Also, in the unlikely event of a fault in the camera system, or other systems in communication with the camera system, the metadata may provide an easy way for the customer service representative to know which serial numbers are involved, and an easy way for the service technician to duplicate the problem by setting up tests under similar conditions.

Without this diagnostic metadata, more time is spent gathering information about issues and/or faults with the system. With the diagnostic metadata embedded, the customer simply provides the picture or video recording that was taken at the time the issue was encountered.

Objects of the invention are achieved by providing a system for diagnosing a medical imaging system that includes an encoding device in communication with an imaging device, which receives medical imaging data from the imaging device and encodes an item of information as metadata; and, an analyzing device which receives the medical image data and the metadata from said encoding device, extracts the item of information from the metadata, and determines whether a problem exists in the system based upon the medical image data and the item of information.

In some implementations, the encoding device receives the item of information from the imaging device. In some implementations, the encoding device receives the information from a system component. The system component may be a head module, a light source, or an imaging device, for example. In some implementations, the analyzing device determines that a problem exists when the item of information deviates from a predetermined range. Optionally, the analyzing device may determine that a problem exists in the system when the image data is reported as faulty and the item of information deviates from a predetermined range.

In some implementations, the analyzing device determines the problem when it is determined that a problem exists. The analyzing device may transmit update information to the imaging device based upon the item of information and the medical imaging data. In some implementations, the item of information is correlated temporally with the image data. Optionally, the metadata is time coded.

The item of information may include a device setting, a software version, a part number, or a sensor reading, for example. Sensor readings may include brightness, illumination, wavelength, shock reading, radiation dose, and temperature readings. Optionally, the item of information may include time or usage information. In some implementations, the imaging data includes video data. Optionally, the metadata is correlated temporally with the image data. Optionally, the analyzing device is in communication with the encoding device. Optionally the analyzing device may communicate with the encoding device over a computer network.

Other objects of the invention are achieved by providing a method for diagnosing a medical imaging system that includes providing an encoding device in communication with an imaging device, which receives medical imaging data from the imaging device and encodes an item of information as metadata; and, providing an analyzing device, which receives the medical image data and the metadata, extracts the item of information from the metadata, and determines whether a problem exists in the system based upon the medical image data and the item of information.

In some implementations, the encoding device receives the item of information from the imaging device. In some implementations, the encoding device receives the information from a system component. The system component may be a head module, a light source, or an imaging device, for example. In some implementations, the analyzing device determines that a problem exists when the item of information deviates from a predetermined range. Optionally, the analyzing device may determine that a problem exists in the system when the image data is reported as faulty and the item of information deviates from a predetermined range.

In some implementations, the analyzing device determines the problem when it is determined that a problem exists. The analyzing device may transmit update information to the imaging device based upon the item of information and the medical imaging data. In some implementations, the item of information is correlated temporally with the image data. Optionally, the metadata is time coded.

The item of information may include a device setting, a software version, a part number, or a sensor reading, for example. Sensor readings may include brightness, illumination, wavelength, shock reading, radiation dose, and temperature readings. Optionally, the item of information may include time or usage information. In some implementations, the imaging data includes video data. Optionally, the metadata is correlated temporally with the image data. Optionally, the analyzing device is in communication with the encoding device. Optionally the analyzing device may communicate with the encoding device over a computer network.

Further objects of the invention are achieved by providing a system for diagnosing a medical imaging system that includes an encoding device having a first processor and a first memory, and in communication with an imaging device, software executing on the first processor for receiving medical imaging data from the imaging device and for encoding an item of information as metadata; and, an analyzing device having a second processor and a second memory, and, software executing on the second processor for receiving the medical image data and the metadata from the encoding device, extracting the item of information from the metadata, and determining whether a problem exists in the system based upon the medical image data and the item of information.

In some implementations, the encoding device receives the item of information from the imaging device. In some implementations, the encoding device receives the information from a system component. The system component may be a head module, a light source, or an imaging device, for example. In some implementations, the analyzing device determines that a problem exists when the item of information deviates from a predetermined range. Optionally, the analyzing device may determine that a problem exists in the system when the image data is reported as faulty and the item of information deviates from a predetermined range.

In some implementations, the analyzing device determines the problem when it is determined that a problem exists. The analyzing device may transmit update information to the imaging device based upon the item of information and the medical imaging data. In some implementations, the item of information is correlated temporally with the image data. Optionally, the metadata is time coded.

The item of information may include a device setting, a software version, a part number, or a sensor reading, for example. Sensor readings may include brightness, illumination, wavelength, shock reading, radiation dose, and temperature readings. Optionally, the item of information may include time or usage information. In some implementations, the imaging data includes video data. Optionally, the metadata is correlated temporally with the image data. Optionally, the analyzing device is in communication with the encoding device. Optionally the analyzing device may communicate with the encoding device over a computer network.

Other objects of the invention and its particular features and advantages will become more apparent from consideration of the following drawings and accompanying detailed description.

DETAILED DESCRIPTION OF THE INVENTION

Figure 1:
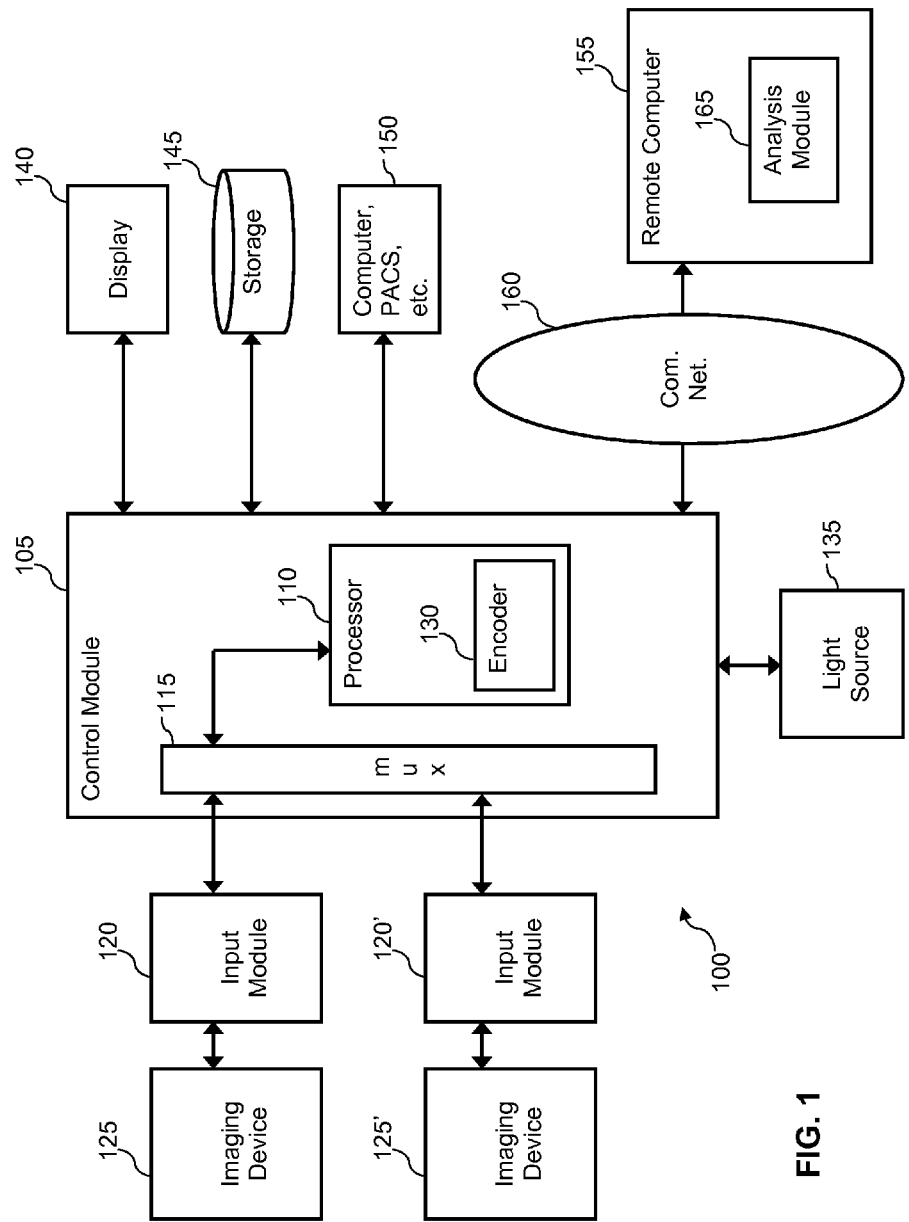
FIG. 1 is a block diagram of an imaging system which illustrates an example implementation of aspects of the invention.

FIG. 1 illustrates an example imaging system 100 according to aspects of the invention.

Imaging system 100 is configured to create processed medical image data, and to correlate metadata regarding the operation of system 100 with the image data in a way that facilitates system diagnostics. The metadata may include information about the structure, configuration, software, or settings of the components of the system, and may include sensor information relating to the state of the components or the environments to which they are exposed. By correlating the metadata with the image data, the cause of various problems with the image data can be analyzed in real time, or subsequent to imaging.

Imaging system 100 may include a control module 105 having a processor 110 and an input multiplexer 115. The control module 105 may also include a memory (not shown) in communication with processor 110, which may include a non-transient computer-readable medium. Software necessary to the operation of the system may be stored on the memory and executed by the processor. Input module 120 connects imaging device 125 to control module 105 via multiplexer 115. Control module 105 is also in communication with various other devices, including display 140, storage 145, computer 150, and remote computer 155. Auxiliary components such as a light source 135 may also be in communication with control module 105.

Control module 105 may be configured to receive image data from various sources, to process the image data, and to output the image data to one or more output devices.

Imaging device 125 may be a camera of the type normally attached to an endoscope as is known in the art, or may be an endoscope having integral image capturing hardware. In principle however, imaging device 125 may be any type of imaging device, such as an ultrasound, x-ray, or CT imager, standard digital camera, or the like. Imaging device 125 may operate according to various parameters, as will be more fully described regarding FIG. 2.

Imaging device 125 communicates with control module 105 via an input module 120 and multiplexer 115; although in some implementations, the imaging device 125 may communicate directly with control module 105.

Input module 120 receives an image signal from imaging device 125 and transmits the image signal to control module 105. Input module 120 may include preprocessing capabilities for adjusting the image signal prior to transmitting the signal to control module 105. For example, input module 120 may provide a color balancing function in order to correct and calibrate the color balance of the imaging device 125. Input module 120 may include a controller or processor (not shown) to perform these preprocessing functions. As with imaging device 125, input module 120 may operate according to various parameters, and will be more fully described regarding FIG. 3.

In some implementations, the communication between input module 120 and imaging device 125 is bi-directional. In such implementations, command signals or other information may be sent from or via input module 120 to imaging device 125. In this way, settings, software, or other data relevant to imaging device 125 can be programmed by or via input module 120, or settings resident in imaging device 125 can be polled by or via input module 120.

Multiplexer 115 facilitates input to control module 105 from multiple imaging sources, such as imaging devices 125 and 125'. In principle, any practical number of input sources of any configuration or having any capabilities may be input in this way. Alternatively, in some implementations control module 105 may accept input from only one image source or otherwise omit multiplexer 115 without departing from the invention. Imaging device 125' and input module 120' may have characteristics and specifications different from imaging device 125 and input module 120. In some implementations, imaging device 125' may be an input from a non-imaging source, such as an image archive, PC, or other source of image data.

The communication between imaging device 125 and control module 105 may be bi-directional. In such implementations, command signals or other signals may be sent from the control module 105 to the input module 120 or to the imaging device 125 via input module 120. In this way, settings of the imaging device 125 or the input module 120 can be programmed by the control module, or information resident in the imaging device 125 or input module 120 can be polled by the control module 105.

Control module 105 includes a processor 110 and an encoder 130. Processor 110 is configured to process imaging data received by control module 105 and to output processed imaging data.

In some implementations, processor 110 converts the image data into a file or streaming format. For example, processor 110 may convert the image data in to a 3G-SDI or HD-SDI format, or a compressed video stream format such as MPEG, which may be transported over an SDI line using the SDTI specification. Alternately, the image data may be converted into a video or image file according to known methods. Many other appropriate stream, file, and compression formats will be evident to those having skill in the art.

In addition to formatting and compression, processor 110 (or in some implementations, a separate module) may provide further image processing functions, such as signal processing, digital image processing, optical and analog image processing, white balance, gamma correction, frame rate conversion, and so forth. Processor 110, or another part of the control module, may also create a GUI, mask, or other graphical overlay to be displayed with the image.

Any or all of these image processing functions may operate according to parameters that are user, factory, or automatically controlled. For example, processor 110 may automatically convert the image data into processed image data having a given frame rate according to a factory setting, or by detecting a frame rate supported or specified by the control module 105. As another example, the processor 110 may automatically correct the color of the image data according to a factory setting, or detected compatibility with control module 105, or the color correction may be specified manually by a user of the system.

After processing, the image data is received by encoder 130. Encoder 130 may receive other information from one or more components of system 100. For example, the various parameters by which imaging device and/or input module 120 operate may be received by encoder 130. Other information that may be relevant to the proper production of an image, such as sensor readings and other recorded data, may also be received by encoder 130. Encoder 130 may encode the received information as metadata.

The relevant information received by encoder 130 for encoding as metadata is typically related to system diagnostics, although other types of data, such as identifying information, may also be included as desired. The particular items of information that are relevant may be specified by the factory or user, or may be automatically specified, and/or otherwise determined in advance.

In addition, in some implementations encoder 130, or another component of control module 105, may be configured to poll elements of system 100 to retrieve all available information, a subset of relevant information, and/or information meeting certain criteria. For example, control module 105 may send a signal to imaging device 125 to request all available sensor information, device settings, software version numbers, or other available information. In the alternative, control module 105 may request a specific subset of this information, such as information considered to be relevant to system diagnostics in a given configuration.

Polling may be conducted directly, or via other components. For example, control module 105 may poll input module 120, which may itself poll image device 125 on behalf of control module 105. In other implementations, components of system 100 automatically provide relevant information to control module 105 without being polled.

By way of example only, information that may be received by encoder 130 may include the properties of any device connected to system 100, such as model number, serial number, installed software, software version, time-in-use/elapsed time, and the like. Such information may also include device settings, such as information relating to exposure, including whether the exposure settings are automatic or manual, gain, shutter speed, focus, diameter, distortion, field of view, endoscope button settings, and/or user settings file contents. Such information may further include processing settings, such as information relating to color correction, white balance, gamma correction, overlay/masking settings, zoom factors, flip/rotate information, focus correction, jitter, motion stabilization, format conversion, frame rate conversion, illumination/LED shutter sync, compression format, compression quality, contrast enhancement, and noise reduction information. Such information may also include sensor readings, such as information relating to temperature, pressure, radiation, shock, light intensity, light frequency, electromagnetic interference, electrostatic discharge, accelerometer, and gyroscope readings.

Examples of other types of information that can be received by encoder 130 from devices attached to system 100 and methods and systems for retrieving this information can be found in U.S. Pat. No. 6,364,827 to Irion et al., U.S. Pat. No. 7,289,139 to Amling et al., U.S. Pat. No. 7,722,531 to Boche, and U.S. Pat. No. 8,194,122 to Amling et al., all of which are incorporated herein by reference in their entirety. For example, part numbers or other information may be retrieved from one or more attached components using a contactless readable data carrier such as an RFID tag or other transponder. It should be noted that communications among the system devices may occur over multiple channels. For example, input module 120 may supply imaging data to control module 105 via one channel, such as a wired connection and may supply other information such as a part number via a separate channel, such as a radio frequency signal or a separate wired connection. Various other suitable arrangements will be evident to those having skill in the art.

The encoder 130 may combine the metadata with the processed image data or transmit it along with the processed image data, depending upon the desired configuration. For example, if the processed image data is formatted by the processor 110 into a 3G-SDI output format, encoder 130 may encode the metadata as "ancillary data" according to that standard. As is known in the art, ancillary data is provided as a standardized transport for non-video payload within a serial digital signal. Many other ways of encoding the parameters as metadata and correlating the metadata with the processed image data according to various open or proprietary standards, or otherwise, will be evident to those having skill in the art.

In the case where the processed image data is video, the metadata can be encoded such that it is synchronized with the frames of the video.

In system 100, encoder 130 is configured as a part of processor 110. However, those having skill in the art will appreciate that encoder 110 may alternately be implemented as a separate hardware and/or software module within control module 105, or a separate module apart from control module 105 without departing from the invention. Furthermore, it will be appreciated that the encoder may be implemented either as a hardware component, or as software stored on the memory (not shown) and executing on processor 110, or on another processing device.

It should be noted that in some implementations, control module 105 may be configured not to perform any further processing on the image data apart from encoding the metadata. In such implementations, the imaging data may be passed unaltered from control module 105, or unaltered except for the addition of metadata. This may be appropriate where imaging device 125 or input module 120 provides imaging data that is already processed and/or in an acceptable format, for example.

Control module 105 is configured to transmit the image data and metadata to various output devices. In example system 100, control module 105 can transmit image data to a display 140, storage 145, or computer 150 (such as a PC, PACS, or other computing device). Control module 105 can also transmit image data and metadata to a remote computer 155. In example system 100, image data and metadata are transmitted via a computer communications network 160. However, in some implementations the image data and metadata may be transferred from control module 105 to remote computer 155 in another way, such as by transfer using a USB key or other portable storage medium. Other ways of transferring the image data and metadata will be evident to those having skill in the art.

Computer communications network 160 may be any communications network or device suitable for facilitating computer communications, such as a LAN, the Internet or a subset thereof.

Remote computer 155 includes an analysis module 165 which is configured to receive the image data and metadata, and to extract the encoded information from the metadata. Analysis module 165 also facilitates troubleshooting of system 100. Analysis module 165 may incorporate a processor, a memory, and software stored on the memory and executed by the processor (not shown). The memory may include a non-transient computer-readable medium.

In an example implementation, remote computer 155 may be situated at the location of a remote technician. If a user of system 100 discovers the image data generated by control module 105 is faulty, the user can send the image data and metadata to remote computer 155. Analysis module 165 may then extract the parameters from the metadata.

In some implementations, the extracted parameters and image data can be manually analyzed by a technician to determine if the problem with the image is a result of any of the parameters. For example, if the image is washed out, the technician may be able to determine if this is due to an incorrect exposure setting in the imaging device 125, input module 120, or control module 105.

Those having skill in the art will appreciate that many variations of this scenario are possible. Examples are provided herein, but those having skill in the art will appreciate that many other permutations of this analysis are possible.

In some implementations, this analysis may be performed automatically by the analysis module 165 without requiring intervention by a technician. For example, if a setting of the imaging device 125 is incompatible with a setting of the input device 120, analysis module 165 may automatically detect this discrepancy. In some implementations, analysis module 165 may also automatically update settings of the imaging device 125, input device 120, or both, in order to resolve the problem.

Enabling remote troubleshooting in this way can have the advantage of reducing the costs and delays that would otherwise be incurred by shipping components to the manufacturer for analysis or by an on-site visit by a technician to diagnose the problem.

In further implementations of system 100, the technician may remotely update the settings in any of the modules connected to control module 105 in order to correct the problem. Optionally, analysis module 165 may be configured to do this automatically, or upon approval by a user.

In some implementations, the troubleshooting cycle can be performed in real time while imaging data from imaging device 125 is streamed to analysis module 165. In this example configuration, settings corrections can be applied during imaging to correct the problem.

Those having skill in the art will appreciate that analysis module 165 may be implemented as a part of control module 105, local computer 150, or as a part of another device (not shown) in communication with control module 105, or that can otherwise receive image data and metadata from control module 105 without departing from the invention.

Figure 2:
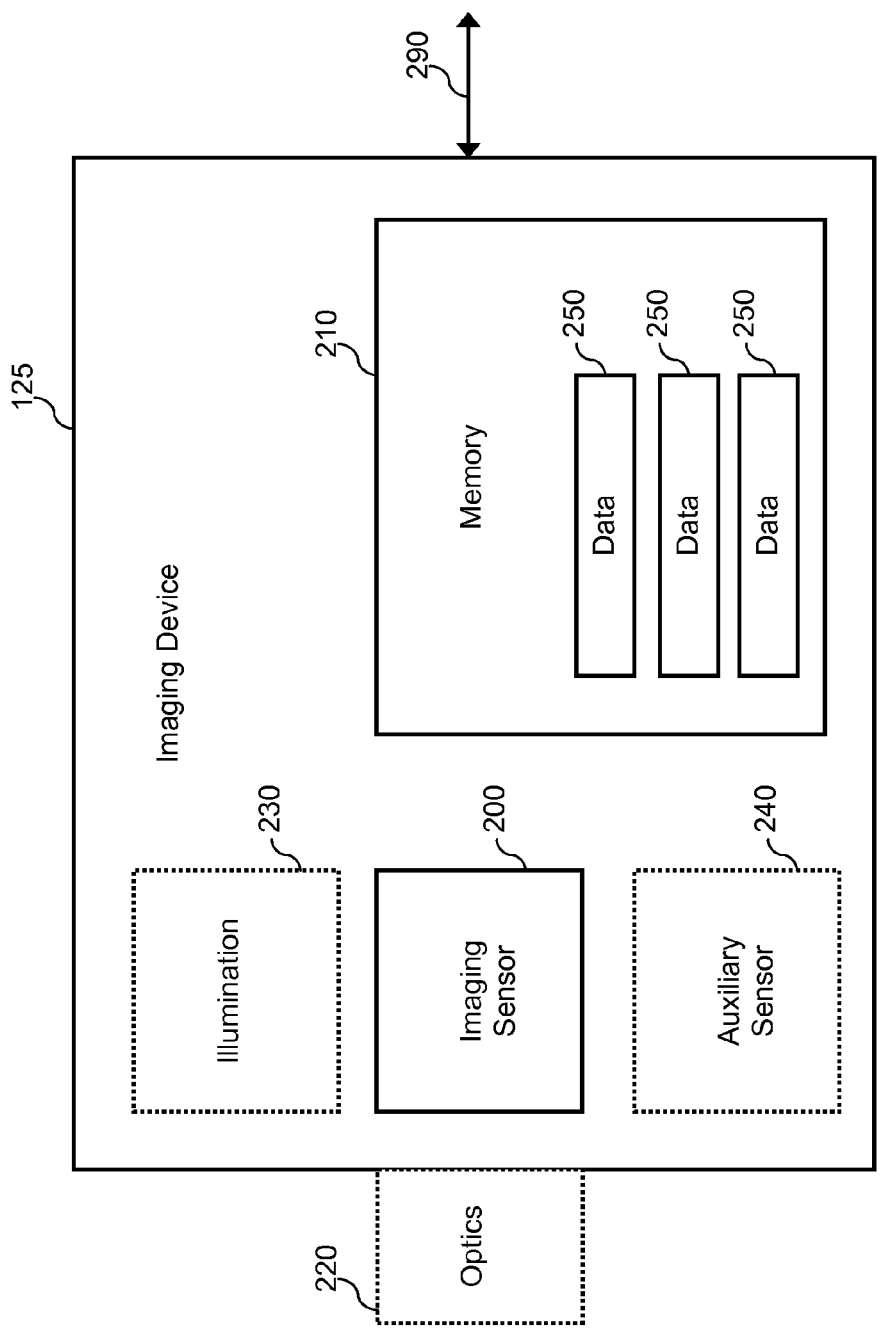
FIG. 2 is a block diagram showing a detail of a portion of the imaging system shown in FIG. 1.

FIG. 2 is a block diagram illustrating example imaging device 125.

Imaging device 125 may include an imaging sensor 200, and a memory 210. Optionally, imaging device may include optics 220, an illumination module 230, an auxiliary sensor 240, and a communications link 290.

Imaging sensor 200 may be a charge-coupled device ("CCD") and any accompanying hardware, or another suitable module for converting light into an electrical signal.

Optics 220 may include one or more lenses, apertures, focusing hardware, or other known optics, which may be manually or mechanically driven.

Illumination 230 may be a light-emitting diode ("LED") light source or other suitable means for illuminating the field of view of the image sensor.

Auxiliary sensor 240 is used to sense environmental conditions other than those sensed by the imaging sensor. For example, Auxiliary sensor 240 may contain a thermometer for sensing temperature, accelerometer for sensing movement and position, Geiger-Müller tube for detecting radiation, and so forth.

Memory 210 stores data 250. Data 250 may include settings for the operation of imaging device 125, or may record information sensed by imaging device 125. For example, data 250 may include settings for focus, exposure, aperture, frame rate, illumination intensity, illumination frequency (i.e. color temperature), and the like. Data 250 may also record temperature, movement, position, radiation, and the like, sensed by auxiliary sensor 240.

Data 250 may also store a device model number and serial number for imaging device 125, as well as software and version information for any software running on the imaging device (not shown). Imaging device 125 may include a processor (not shown) executing software if this is necessary or desired for any function of imaging device 125. This software (not shown) may be stored on memory 210, or another memory in communication with the processor.

Data 250 may also or alternatively be stored in a memory that is not a part of imaging device 125. For instance, imaging device 125 may access parameters stored in input module 120, control module 105, or another component in communication with control module 105. In some configurations, imaging device 125 may omit memory 210.

Some or all of data 250 may be received as information by the encoder 130, as described above.

Figure 3:
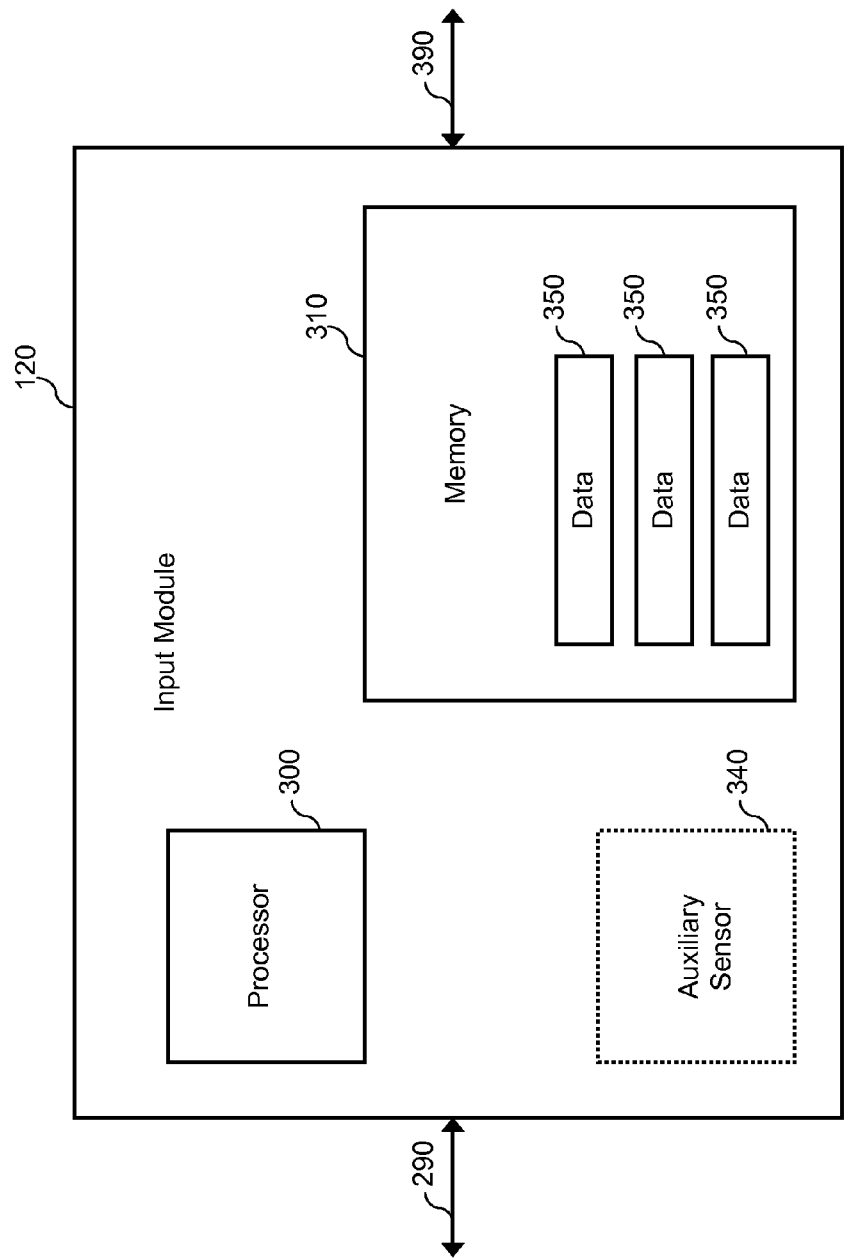
FIG. 3 is a block diagram showing another detail of a portion of the imaging system shown in FIG. 1.

FIG. 3 is a block diagram illustrating example input module 120.

Input module 120 may include a processor 300 and a memory 310. Optionally, input module 120 may include an auxiliary sensor 340. Input module 120 may receive image data from imaging device 125 via a communications link 290. Control module 105 may receive some or all of data 250, data 350, and/or image data via a communications link 390.

Processor 300 may be is used to perform preprocessing operations on the image data. For example, the input module may convert the image data into a format that is readable by control module 105. Processor 300 may also perform other types of preprocessing on the image data, including signal processing, digital image processing, optical and analog image processing, white balance, gamma correction, frame rate conversion, and other preprocessing tasks known in the art.

Any or all of these image processing functions may operate according to parameters that are user, factory, or automatically controlled. For example, processor 300 may automatically convert the image data to a different frame rate or resolution. As another example, the processor 300 may automatically correct the color of the image data, or the color correction may be specified manually by a user of the system.

Memory 310 stores data 350. Data 350 may include settings for the operation of input module 120, or may record information sensed by input module 120. For example, data 250 may include settings for frame rate, resolution, color correction, and the like. Data 350 may also record environmental information sensed by auxiliary sensor 340.

Data 350 may also store a device model number and serial number for input module 120, as well as software and version information for any software running on the input module 120 (not shown). Processor 300 may execute software (not shown) if this is necessary or desired for any function of input module 120, and this software may be stored on memory 310, or another memory in communication with processor 300.

Data 250 may also or alternatively be stored in a memory that is not a part of input module 120. For instance, input module 120 may access parameters stored in imaging device 125, control module 105, or another component in communication with control module 105. In some configurations, input module 120 may omit memory 310.

Some or all of data 350 may be received as information by the encoder 130, as described above.

Figure 4:
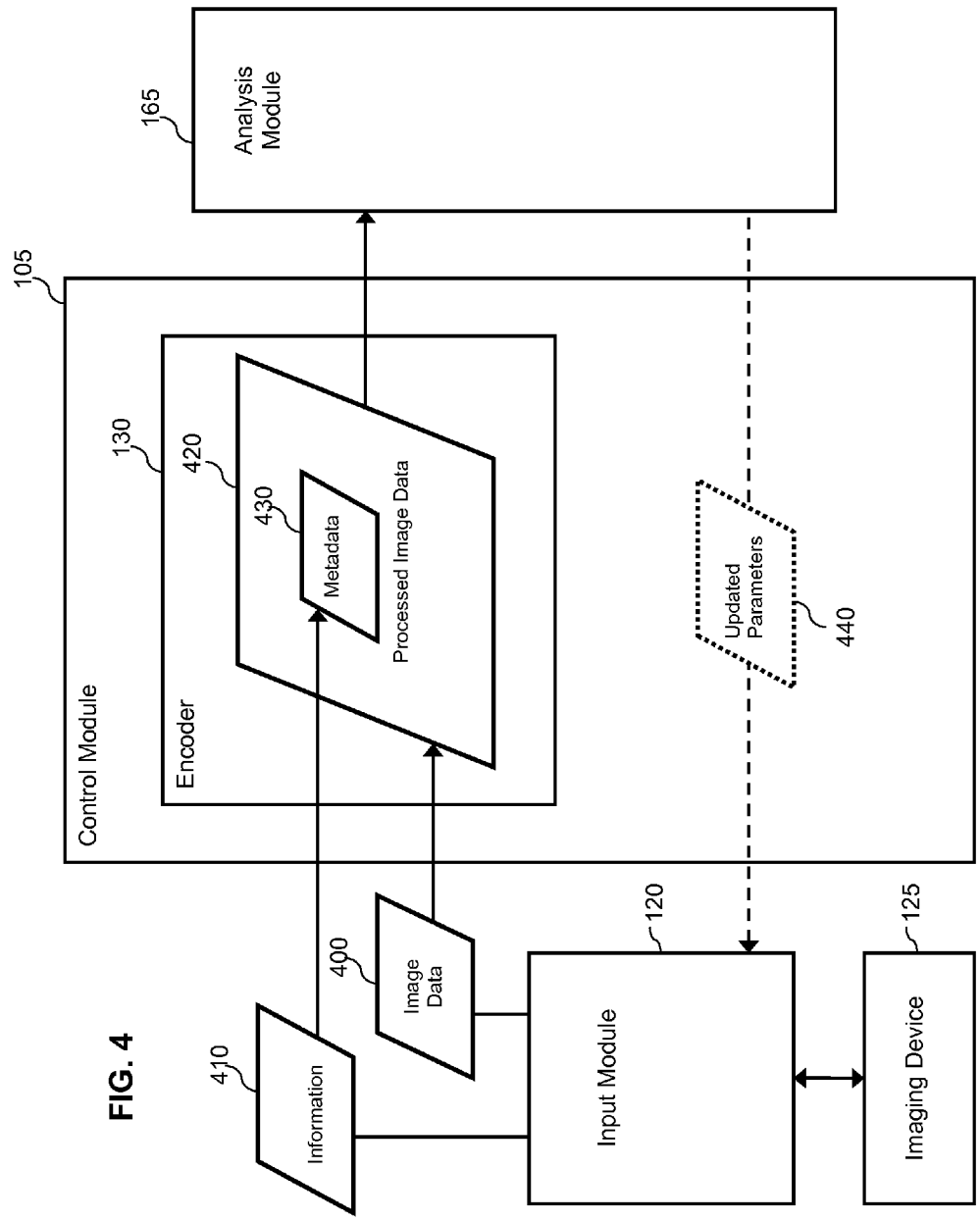
FIG. 4 is a block diagram showing an example data flow among components of the imaging system shown in FIG. 1.

FIG. 4 is a simplified block diagram illustrating an example data flow within system 100. For clarity, only those components of system 100 that conveniently illustrate the data flow are represented.

In FIG. 4, imaging device 125 supplies image data 400 and information 410 to control module 105 via input module 120. Image data 400 may or may not be pre-processed by input module 120. Information 410 may include data 250, 350 or other information. Information 410 may be transmitted once, upon a change in the information, or may be transmitted continuously or synchronously with the image data 400. In addition, some of the parameters may be transmitted in one of these ways, while others are transmitted differently.

Control module 105 may further process image data 400 and may supply additional information 410 relating to control module 105 or other components in communication with control module 105.

Encoder 130 receives the processed image data 420 and information 410, and encodes information 410 as metadata 430. As shown in FIG. 4, metadata 430 is encapsulated within processed image data 420 by encoder 130. The encapsulation may be according to any known metadata standard. In alternative implementations, the metadata may be transmitted in an unencapsulated fashion, or encoded in a different way. Optionally, the metadata may be transmitted separately from the image data.

Analysis module 165 receives processed image data 420 and metadata 430, and extracts the information 410 from the metadata 430, and analyzes the image data 420 and image data 420 to determine if there is a problem with system 100. This analysis can be conducted in a number of different ways, depending on the desired implementation. For example analysis module 165 may be monitored by a technician who can view the image data 420 and the information 410, and make a determination as to whether there is a problem with system 100, and how and whether it is possible to correct the problem. For example, if information 410 includes the color correction settings of the input module, and the image appears incorrectly colored, the technician may infer that the color correction settings need to be adjusted. In some implementations, the technician can transmit updated parameters 440 to the input module to correct the problem.

In other implementations, the technician is replaced by an automated system such as a software functionality incorporated into analysis module 165 that can perform these tasks. For example, in the scenario above an incorrect color balance may be automatically detected by image analysis software, and an adjustment may be automatically calculated based upon the color balance detected in image data 420 and the color correction information from information 410.

The example scenario above is not intended to be limiting, and many image analysis and correction scenarios will be evident to those having skill in the art by reference to the disclosures herein.

Further, in some implementations, analysis module may infer that there is a problem with the image based upon having received it. This configuration may be appropriate where, for example, a user of system 100 only sends data to the analysis module when the user is dissatisfied with the image. In this case, analysis module 165 may proceed directly to determining what the problem is. In other implementations, the analysis module may detect whether there is a problem before determining the nature of the problem. This may be appropriate where the analysis module is receiving a continuous feed of image data 420 and metadata 430, or is analyzing a moving image file where a problem only exists in portions of the video.

It should be noted that although in examples herein diagnostics information is transmitted via metadata, various other data may be transferred among elements of system 100 in other ways. For example, relevant information may be transmitted from imaging device 125 to control module 105 separately from the image data and/or via sideband signaling, such as via an RFID transceiver arrangement (not shown).

Although the invention has been described with reference to a particular arrangement of parts, features and the like, these are not intended to exhaust all possible arrangements or features, and indeed many modifications and variations will be ascertainable to those of skill in the art.

What is claimed is:

1. A system for diagnosing a medical imaging system, comprising:
an input module connected to an imaging device, the input module receiving medical imaging data from the imaging device and being configured to process the medical imaging data;
a control module connected to the input module and receiving the medical imaging data from the input module, the control module being configured to control the imaging device via the input module, the input module being configured to send command signals to the imaging device;
the control module having an encoding device, the encoding device receives the medical imaging data, the encoding device polls at least two system components of the medical imaging system for retrieval of an item of information from each of the at least two system components by sending a signal which requests information of the at least two system components, wherein the at least two system components include the imaging device and the input module, and the encoding device encodes the items of information as metadata within the medical imaging data, wherein the items of information include device settings; and,
an analyzing device, which receives the medical imaging data and the metadata from said encoding device of said control module, extracts the items of information from the metadata, and determines whether a problem exists in the medical imaging system based upon the medical imaging data and the items of information.

2. The system of claim 1, wherein the at least two system components include a head module.

3. The system of claim 1, wherein the at least two system components include a light source.

4. The system of claim 1, wherein the analyzing device determines that a problem exists when one of the items of information deviates from a predetermined range.

5. The system of claim 1, wherein the analyzing device determines that a problem exists in the system when the imaging data is reported as faulty and one of the items of information deviates from a predetermined range.

6. The system of claim 1, wherein the analyzing device determines the problem when it is determined that a problem exists.

7. The system of claim 1, wherein the analyzing device transmits update information to the imaging device based upon the items of information and the medical imaging data.

8. The system of claim 1, wherein the items of information are correlated temporally with the imaging data.

9. The system of claim 1, wherein the metadata is time coded.

10. The system of claim 1, wherein the items of information comprise a software version.

11. The system of claim 1, wherein the items of information comprise a part number.

12. The system of claim 1, wherein the items of information comprise a sensor reading.

13. The system of claim 12, wherein the sensor reading is selected from the group consisting of brightness, illumination, wavelength, shock reading, radiation dose, and temperature.

14. The system of claim 1, wherein the items of information comprise time information.

15. The system of claim 1, wherein the items of information comprise usage information.

16. The system of claim 1, wherein the imaging data comprises video data.

17. The system of claim 1, wherein the metadata is correlated temporally with the imaging data.

18. The system of claim 1, wherein the analyzing device is in communication with the encoding device.

19. The system of claim 1, wherein the analyzing device communicates with the encoding device over a computer communications network.

20. A method for diagnosing a medical imaging system, comprising:
providing an input module that connects to an imaging device and is configured to receive medical imaging data from the imaging device and process the medical imaging data;
providing a control module that connects to the input module and is configured to receive the medical imaging data from the input module and control the imaging device via the input module, the input module being configured to send command signals to the imaging device;
providing an encoding device within the control module, the encoding device receives the medical imaging data, the encoding device polls at least two system components of the medical imaging system for retrieval of an item of information from each of the at least two system components by sending a signal which requests information of the at least two system components, wherein the at least two system components include the imaging device and the input module, and the encoding device encodes the items of information as metadata within the medical imaging data, wherein the items of information include device settings; and,
providing an analyzing device, which receives the medical imaging data and the metadata from said encoding device of said control module, extracts the items of information from the metadata, and determines whether a problem exists in the medical imaging system based upon the medical imaging data and the items of information.

21. The method of claim 20, wherein the at least two system components include a head module.

22. The method of claim 20, wherein the at least two system components include a light source.

23. The method of claim 20, wherein the analyzing device determines that a problem exists when one of the items of information deviates from a predetermined range.

24. The method of claim 20, wherein the analyzing device determines that a problem exists in the system when the imaging data is reported as faulty and one of the items of information deviates from a predetermined range.

25. The method of claim 20, wherein the analyzing device determines the problem when it is determined that a problem exists.

26. The method of claim 20, wherein the analyzing device transmits update information to the imaging device based upon the items of information and the medical imaging data.

27. The method of claim 20, wherein the items of information are correlated temporally with the imaging data.

28. The method of claim 20, wherein the metadata is time coded.

29. The method of claim 20, wherein the items of information comprise a software version.

30. The method of claim 20, wherein the items of information comprise a part number.

31. The method of claim 20, wherein the items of information comprise a sensor reading.

32. The method of claim 31, wherein the sensor reading is selected from the group consisting of brightness, illumination, wavelength, shock reading, radiation dose, and temperature.

33. The method of claim 20, wherein the items of information comprise time information.

34. The method of claim 20, wherein the items of information comprise usage information.

35. The method of claim 20, wherein the imaging data comprises video data.

36. The method of claim 20, wherein the metadata is correlated temporally with the imaging data.

37. The method of claim 20, wherein the analyzing device is in communication with the encoding device.

38. The method of claim 20, wherein the analyzing device communicates with the encoding device over a computer network.

39. A system for diagnosing a medical imaging system, comprising:
an input module connected to an imaging device, the input module receiving medical imaging data from the imaging device and being configured to process the medical imaging data,
a control module connected to the input module and receiving the medical imaging data from the input module, the control module being configured to control the imaging device via the input module, the input module being configured to send command signals to the imaging device,
the control module having an encoding device which has a first processor and a first memory,
software executing on the first processor to receive the medical imaging data, to poll at least two system components of the medical imaging system for retrieval of an item of information from each of the at least two system components by sending a signal which requests information of the at least two system components, wherein the at least two system components include the imaging device and the input module, and to encode the items of information as metadata within the medical imaging data, wherein the items of information include device settings,
an analyzing device having a second processor and a second memory, and,
software executing on the second processor to receive the medical imaging data and the metadata from the encoding device of said control module, to extract the items of information from the metadata, and to determine whether a problem exists in the medical imaging system based upon the medical imaging data and the items of information.

40. The system of claim 39, wherein the at least two system components include a head module.

41. The system of claim 39, wherein the at least two system components include a light source.

42. The system of claim 39, wherein the analyzing device determines that a problem exists when one of the items of information deviates from a predetermined range.

43. The system of claim 39, wherein the analyzing device determines that a problem exists in the system when the imaging data is reported as faulty and one of the items of information deviates from a predetermined range.

44. The system of claim 39, wherein the analyzing device determines the problem when it is determined that a problem exists.

45. The system of claim 39, wherein the analyzing device transmits update information to the imaging device based upon the items of information and the medical imaging data.

46. The system of claim 39, wherein the items of information are correlated temporally with the imaging data.

47. The system of claim 39, wherein the metadata is time coded.

48. The system of claim 39, wherein the items of information comprise a software version.

49. The system of claim 39, wherein the items of information comprise a part number.

50. The system of claim 39, wherein the items of information comprise a sensor reading.

51. The system of claim 50, wherein the sensor reading is selected from the group consisting of brightness, illumination, wavelength, shock reading, radiation dose, and temperature.

52. The system of claim 39, wherein the items of information comprise time information.

53. The system of claim 39, wherein the items of information comprise usage information.

54. The system of claim 39, wherein the imaging data comprises video data.

55. The system of claim 39, wherein the metadata is correlated temporally with the imaging data.

56. The system of claim 39, wherein the analyzing device is in communication with the encoding device.

57. The system of claim 39, wherein the analyzing device communicates with the encoding device over a computer communications network.

58. The system of claim 1, wherein the medical imaging data is video and the items of information are encoded to be synchronized with frames of the video.

59. The method of claim 20, wherein the medical imaging data is video and the items of information are encoded to be synchronized with frames of the video.

60. The system of claim 39, wherein the medical imaging data is video and the items of information are encoded to be synchronized with frames of the video.

* * * * *